(12) United States Patent
Kii

(10) Patent No.: US 12,339,415 B2
(45) Date of Patent: Jun. 24, 2025

(54) ELECTRONIC DEVICE, STORAGE MEDIUM AND TERRAIN SENSING METHOD

(71) Applicant: CASIO COMPUTER CO., LTD., Tokyo (JP)

(72) Inventor: Takehiko Kii, Tokyo (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 317 days.

(21) Appl. No.: 17/894,883

(22) Filed: Aug. 24, 2022

(65) Prior Publication Data

US 2023/0081304 A1  Mar. 16, 2023

(30) Foreign Application Priority Data

Sep. 16, 2021 (JP) .................................. 2021-150780

(51) Int. Cl.
*G01V 20/00* (2024.01)
*G01C 21/16* (2006.01)
*G06N 20/00* (2019.01)

(52) U.S. Cl.
CPC ............ *G01V 20/00* (2024.01); *G01C 21/16* (2013.01); *G06N 20/00* (2019.01)

(58) Field of Classification Search
CPC ........ G01V 20/00; G01C 21/16; G06N 20/00; A61B 5/1116; A61B 5/1122
See application file for complete search history.

(56) References Cited

U.S. PATENT DOCUMENTS

| | | | |
|---|---|---|---|
| 2014/0142466 A1* | 5/2014 | Kawabe | A61B 5/112 600/595 |
| 2014/0180173 A1* | 6/2014 | Sullivan | A61B 5/112 600/595 |
| 2014/0195018 A1 | 7/2014 | Kang et al. | |
| 2016/0206242 A1 | 7/2016 | Esposito et al. | |
| 2022/0211297 A1 | 7/2022 | Huang et al. | |

FOREIGN PATENT DOCUMENTS

| | | | |
|---|---|---|---|
| JP | 2008302746 A | 12/2008 | |
| JP | 2013017615 A | 1/2013 | |
| JP | 2013255608 A | 12/2013 | |
| JP | 2017023689 A | 2/2017 | |
| JP | 2018079102 A | 5/2018 | |
| JP | 2020005766 A | 1/2020 | |
| WO | WO-2014087166 A1 * | 6/2014 | ............ G01C 21/20 |
| WO | 2020240749 A1 | 12/2020 | |

OTHER PUBLICATIONS

Japanese Office Action (and an English language translation thereof) dated Oct. 3, 2023, issued in counterpart Japanese Application No. 2021-150780.
Extended European Search Report (EESR) dated Feb. 8, 2023, issued in counterpart European Application No. 22195348.2.
Jitpakdee, et al., "Neural networks terrain classification using Inertial Measurement Unit for an autonomous vehicle", Sice Annual Conference, 2008, IEEE, Piscataway, NJ, USA, XP031351187, pp. 554-558.

* cited by examiner

*Primary Examiner* — Manuel A Rivera Vargas
(74) *Attorney, Agent, or Firm* — Holtz, Holtz & Volek PC

(57) ABSTRACT

An electronic device includes a processing unit which acquires body motion information of a user during a movement action by the user, and determines terrain while the user is moving based on the body motion information acquired.

17 Claims, 9 Drawing Sheets

ELECTRONIC DEVICE, STORAGE MEDIUM AND TERRAIN SENSING METHOD

This application is based on and claims the benefit of priority from Japanese Patent Application No. 2021-150780, filed on 16 Sep. 2021, the content of which is incorporated herein by reference.

BACKGROUND OF THE INVENTION

Field of the Invention

The present invention relates to an electronic device, storage medium and a terrain sensing method.

Description of the Related Art

Conventionally, technology for acquiring and evaluating body motion information of a user during a movement action has been known. As documents in which this type of technology is disclosed, for example, there is Japanese Unexamined Patent Application, Publication No. 2020-5166. In Japanese Unexamined Patent Application, Publication No. 2020-5766, a device is disclosed which performs machine learning with movement data of a user, self-evaluation data and GPS data as training data, and predicts and calculates self-evaluation related to new motion data.

In Patent Document 1, a running form of the user, etc. is evaluated using various data such as motion data and terrain data; however, there has been room for improvement in the point of acquiring the topographic data from a database or the like, and acquiring more detailed information of terrain on which the user is moving.

The present invention has been made taking account of such a situation, and has an object of providing an electronic device, storage medium and terrain sensing method which can determine the terrain on which a user is moving with high precision.

SUMMARY OF THE INVENTION

The present invention provides an electronic device including a processing unit which acquires body motion information of a user during a movement action by the user; and determines terrain during movement by the user based on the body motion information acquired. In addition, the present invention provides a non-transitory computer-readable storage medium storing a program that is executed by a computer that comprises a processor to control an electronic device, the program being executable to cause the computer to perform operations of acquiring body motion information of a user during a movement action by the user; and determining terrain during movement by the user based on the body motion information acquired. Furthermore, the present invention provides a terrain sensing method executed by an electronic device, the method including: acquiring body motion information of a user during a movement action by the user; and determining terrain during movement by the user based on the body motion information acquired.

DETAILED DESCRIPTION OF THE PREFERRED EMBODIMENT

Hereinafter, an embodiment of the present invention will be explained using the drawings.

Terrain Sensing System

Figure 1:
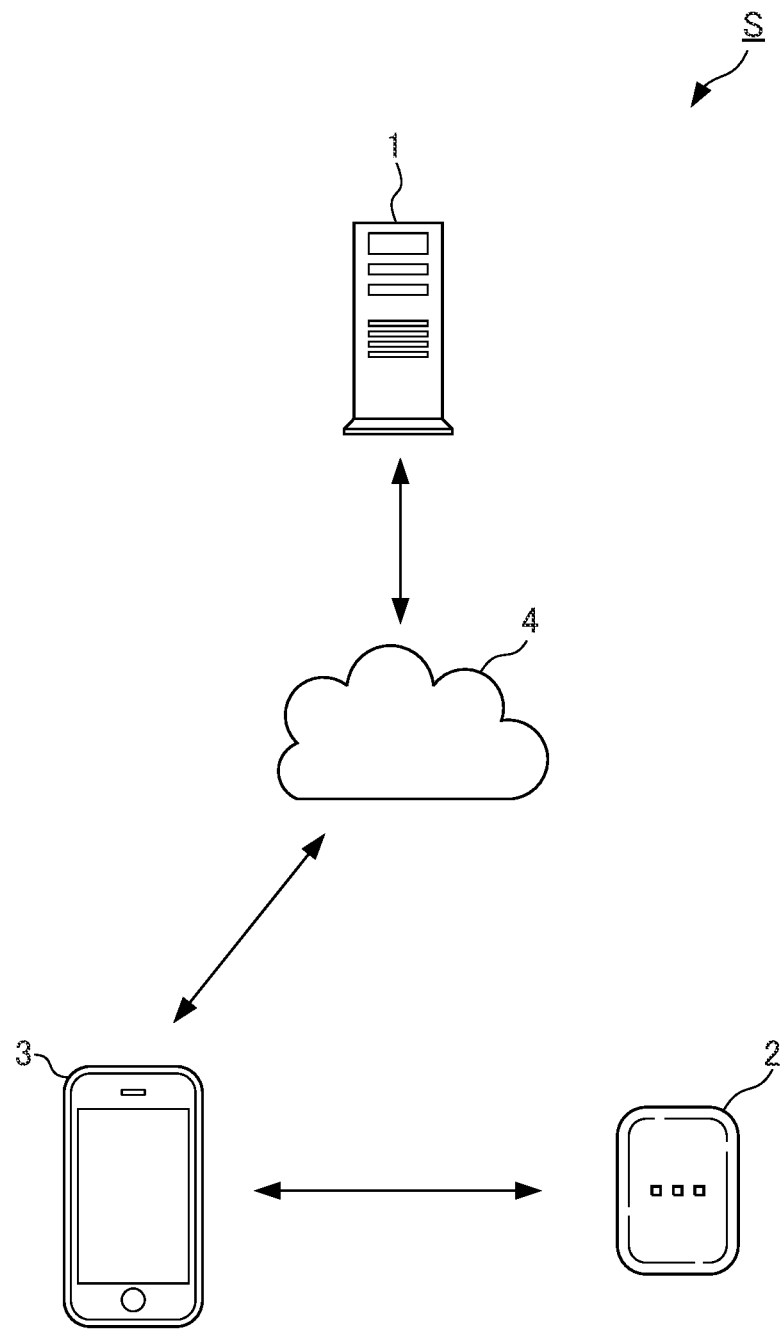
FIG. 1 is a system configuration drawing showing the configuration of a terrain sensing system according to an embodiment of the present invention.

FIG. 1 is a system configuration diagram showing a terrain sensing system S according to an embodiment of the present invention. As shown in FIG. 1, the terrain sensing system S includes a management server 1 as electronic devices performing terrain sensing processing, a sensor device 2 and a user terminal 3.

The management server 1 and user terminal 3 can communicate with each other. Communication between the management server 1 and user terminal 3, for example, is realized by any of the internet, LAN (Local Area Network) and a portable telephone network or a network 4 made by combining these. In addition, the user terminal 3 and sensor device 2 can also communication with each other. Communication between the user terminal 3 and sensor device 2, for example, is performed by BLE (Bluetooth (registered trademark) Low Energy). It should be noted that the communication system is an exemplification, and communication between the management server 1 and user terminal 3 and communication between the user terminal 3 and sensor device 2 may user another communication system.

The sensor device 2 has a sensing function of sensing body motion of the user when this user performs a movement action such as walking or running; a positioning function of measuring the position of the sensor device 2; and a communication function of sending a sensing result to the user terminal 3. Hereinafter, various data acquired by the sensor device 2 will be explained by calling log data.

Figure 2:
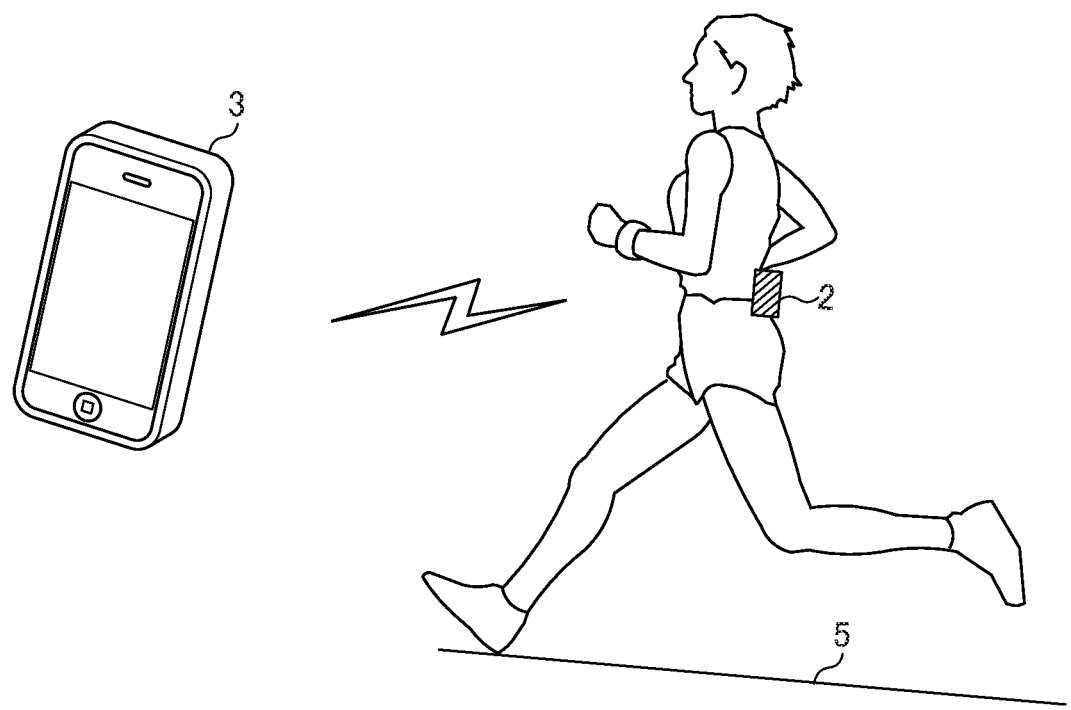
FIG. 2 is a schematic diagram showing a use example of a sensor device according to an embodiment of the present invention.

A use example of the sensor device 2 will be explained. FIG. 2 is a schematic diagram showing a use example of the sensor device 2 according to the embodiment of the present invention. As shown in FIG. 2, the sensor device 2 of the present embodiment is worn close to the waist at a position along the trunk of the user performing a predetermined movement action on a ground surface 5 (although the present embodiment explains a case of walking or running, the movement action is not limited thereto).

The sensor device 2 acquires movement data such as a change of movement speed (acceleration) during walking or during running of the user, change in movement direction (angular speed), or the like by the sensing function. The sensor device 2 acquires the positioning data such as movement trajectory or travel distance when a user performed an activity such as walking or running by the positioning function. Hereinafter, data including movement data and positioning data acquired by the sensor device 2 will be explained by calling log data. In addition to the movement distance, the posture during movement, etc. may be calibrated using the angle formed by the gravitational acceleration and the axis of the longitudinal direction (predetermined direction) of the sensor device 2.

The user terminal 3 is a communication device having a calculation processing function and communication function. The user terminal for example, is realized by a wearable device such as a smartphone, tablet or smart match which are portable by the user.

The user terminal 3 of the present embodiment has a communication function receiving log data from the sensor device 2, sending this to the management server 1, and receiving information from the management server 1; a positioning function of measuring the position of the user terminal 3; and an output function of outputting to display analysis results of log data by the management server 1. By the output function of the user terminal it is possible for the user to understand the analysis results of the sensor information in a simple and intuitively recognizable format.

The management server 1 is a management device having a calculation processing function and communication function. The management server 1 is realized by the server vice or an electronic device such as personal computer, for example. The management server 1 acquires the body motion information or the user based on the log data sent from the sensor device via the user terminal 3, and determines the terrain on which the user is moving. In addition, the management server 1 acquires route information including information such as altitude, latitude, longitude information of the route on which the user moved by analyzing the positioning data, and corrects this route information as needed. The body motion information, route information, analysis results of terrain, etc. acquired by the management server 1 are sent to the user terminal 3 it should be noted that the management server 1 is configured to be able to receive log data from a plurality of the sensor devices 2 via a plurality of the user terminals 3.

Hardware Configuration

Figure 3:
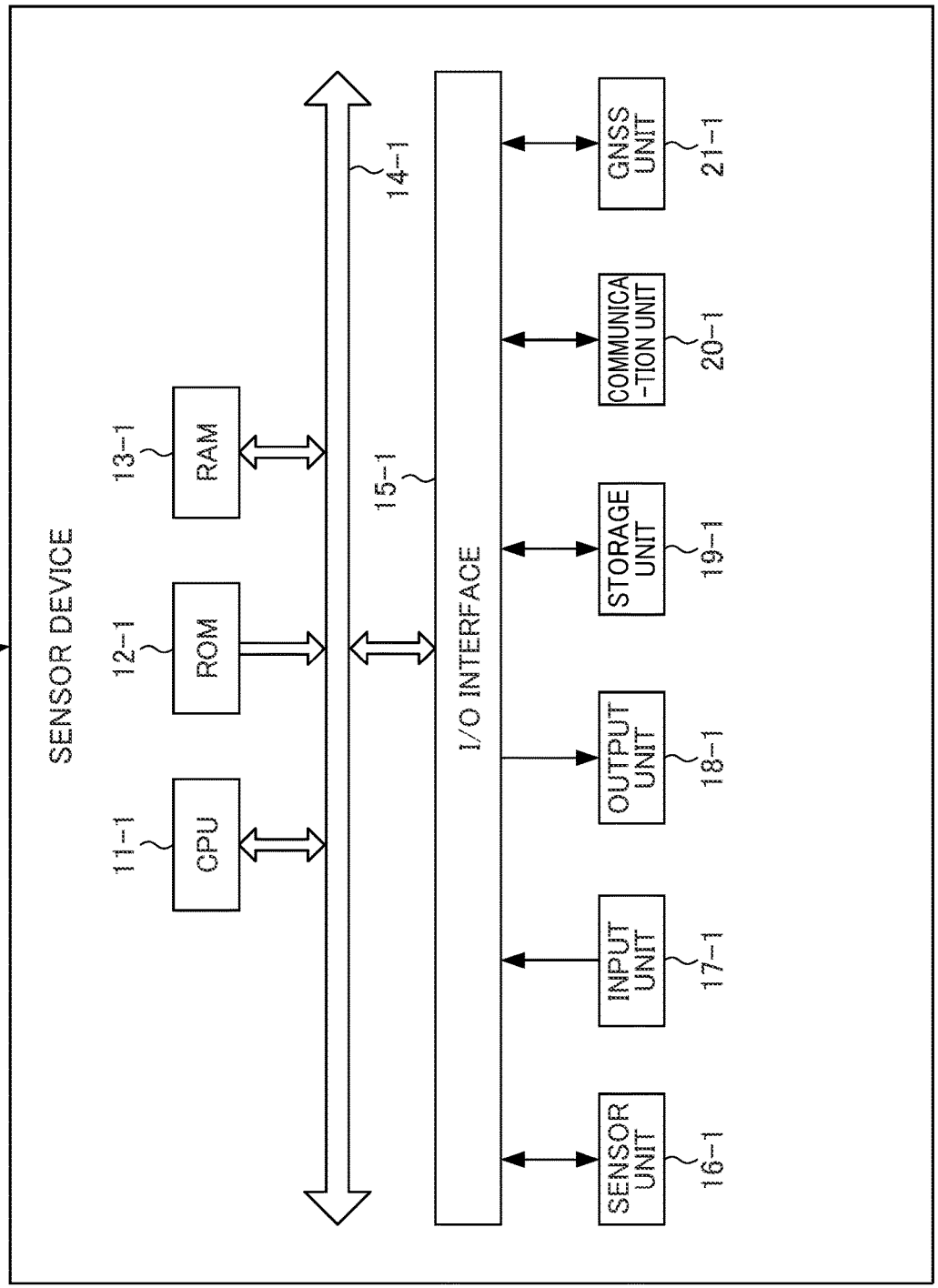
FIG. 3 is a block diagram showing the configuration of hardware of a sensor device according to an embodiment of the present invention.

Next, an example of the configuration of the hardware of the sensor device 2 will be explained. FIG. 3 is a block diagram showing the configuration of the hardware of the sensor device 2 according to the embodiment of the present invention. As shown in FIG. 3, the sensor device includes a CPU (Central Processing Unit) 11-1, ROM (Read Only Memory) 12-1, RAM (Random Access Memory) 13-1, bus 14-1, I/O interface 15-1, sensor unit 16-1, input unit 17-1, output unit 18-1, storage unit 19-1, communication unit 20-1, and GNSS unit 21-1.

The CPU 11-1 executes various processing in accordance with a program recorded in the ROM 12-1, or program loaded in the RAM 13-1 from the storage unit 19-1.

The necessary data, etc. upon the CPU 11-1 executing various processing is also stored as appropriate in the RAM 13-1.

The CPU 11-1, ROM 12-1 and RAM 13-1 are connected with each other via the bus 14-1. This bus 14-1 is also connected to the I/O interface 15-1. The sensor unit 16-1, input unit 17-1, output unit 18-1, storage unit 19-1 communication unit 20-1 and GNSS unit 21-1 are connected to the I/O interface 15-1.

The input unit 17-1 is configured by various buttons, etc., and inputs various information according to the instruction operation of the user.

The output unit 18-1 is configured by an LED (Light Emitting Diode) lamp, display speakers, etc., and outputs light, images, sound, etc.

The storage unit 19-1 is configured by hard disk, flash memory or the like, and stores various data.

The communication unit 20-1, for example, controls communication performed with other devices by wireless such as BLE (Bluetooth (registered trademark) Low Energy) wire such as USB.

The sensor unit 16-1 is configured from an acceleration sensor and/or gyrosensor for measuring the position of three-dimensional motion of the sensor device 2 itself. The accelerator sensor is a device which detects movement and acceleration in any direction. For example, the acceleration sensor is a three-axis sensor of capacitance type or piezo resistance element type, and detects acceleration generated in each of the three-axis directions orthogonal to each other. The gyrosensor is a device detecting the movement in any direction and the angular speed. For example, the gyrosensor is a three-axis sensor of capacitance type or piezo resistance element type, and detects angular speed generated in each of the three-axis directions orthogonal to each other.

The sensor unit 16-1 at least detects the acceleration and angular speed imparted on the sensor device 2 in response to the movement of the user wearing the sensor device 2, and stores in the storage unit 19-1 as log data. The log data is sent to the user terminal 3 via the communication unit 20-1 afterwards, and is sent to the management server 1 via the user terminal 3. The management server 1 acquires the body motion information of the user wearing the sensor device 2 by analyzing the received log data. In the present embodiment, the start and end of sensing are performed with the trigger of a user operation on the input unit 17-1.

The GNSS unit 21-1 performs positioning based on positioning satellite signals sent from positioning satellites. GNSS is an abbreviation of Global Navigation Satellite System, and the GNSS unit 21-1 uses a satellite measurement system such as GPS. The GNSS unit 21-1 of the present embodiment includes an antenna, receives positioning satellite signals from a plurality of positioning satellites, and sends the received positioning satellite signals to the CPU 11-1. The CPU 11-1 acquires the positioning data including positional information of the sensor device 2, based on the positioning satellite signals received from the GNSS unit 21-1.

It should be noted that the sensor device 2, in addition to the above exemplified configuration, may include a drive into which is installed as appropriate removable media such as a magnetic disk, optical disk, magneto-optical disk or semiconductor memory. The program and/or data read from a removable medium by the drive is installed to the storage unit 19-1 as necessary.

Figure 4:
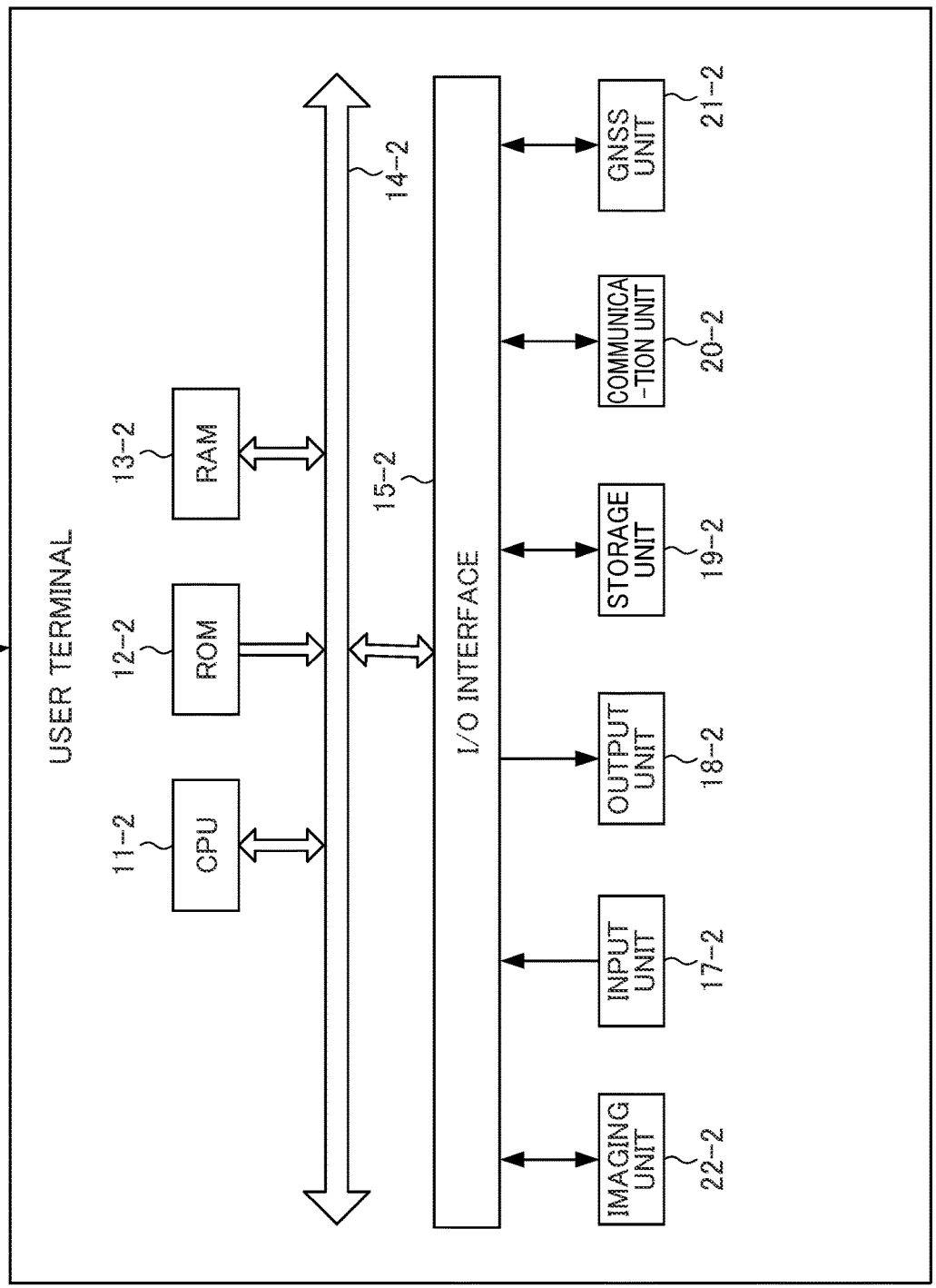
FIG. 4 is a block diagram showing the configuration of hardware of a user terminal according to an embodiment of the present invention.

Next, the hardware configuration of the user terminal 3 will be explained. FIG. 4 is a block diagram showing the configuration of hardware of the user terminal 3 according to the embodiment of the present invention. As shown in FIG. 4, the user terminal 3 includes a CPU 11-2, ROM 12-2, RAM 13-2, bus 14-2, I/O interface 15-2, input unit 17-2, output unit 18-2, storage unit 19-2, communication unit 20-2, GNSS unit 21-2 and imaging unit 22-2. For the user terminal 3, explanations of configurations which are similar to the sensor device 2 will be omitted.

The input unit 17-2 and output unit 18-2 are user interfaces connected to the I/O interface 15-2 electrically either by wire or wirelessly. The input unit 17-2 is configured by a keyboard or mouse, various buttons, microphone, etc., for example, and inputs various information according to an instruction operation of the user. The output unit 18-2 is configured by a display displaying images, a speaker amplifying speech, etc., and outputs images and speech.

The imaging unit 22-2, although not illustrated, includes an optical lens, unit, and image sensor. The data of captured images captured by the imaging unit 22-2 is suppled as appropriate to the CPU 11-2, an image processing unit not illustrated, or the like.

Figure 5:
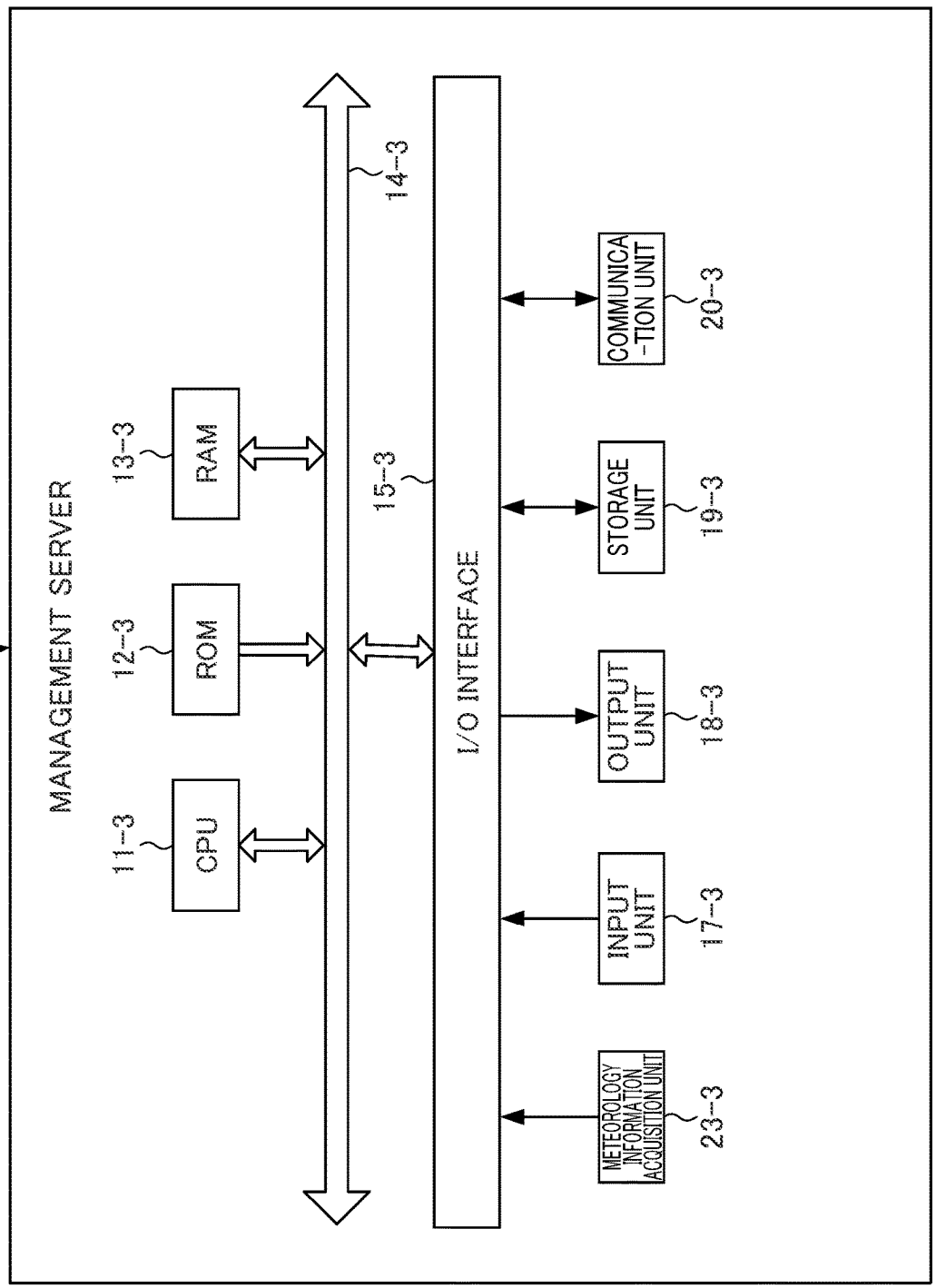
FIG. 5 is a block diagram showing the configuration of hardware of a management server according to an embodiment of the present invention.

Next, a hardware configuration of the management server will be explained. FIG. 5 is a block diagram showing the configuration of hardware of the management server 1 according to the embodiment of the present invention. As shown in FIG. 5, the management server 1 includes a CPU 11-3, ROM 12-3, RAM 13-3, bus 14-3, I/O interface 15-3, input unit 17-3, output unit 18-3, storage unit 19-3, communication unit 20-3, and meteorology information acquisition unit 23-3. For the management server explanations will be omitted for configurations similar to the sensor device 2.

The meteorology information acquisition unit 23-3 acquires weather information from a weather data collection system such as AMeDAS, or the like, via the communication unit 20-3. Weather information such as clear skies, cloudy, rain or snow is included in the meteorology information.

Figure 6:
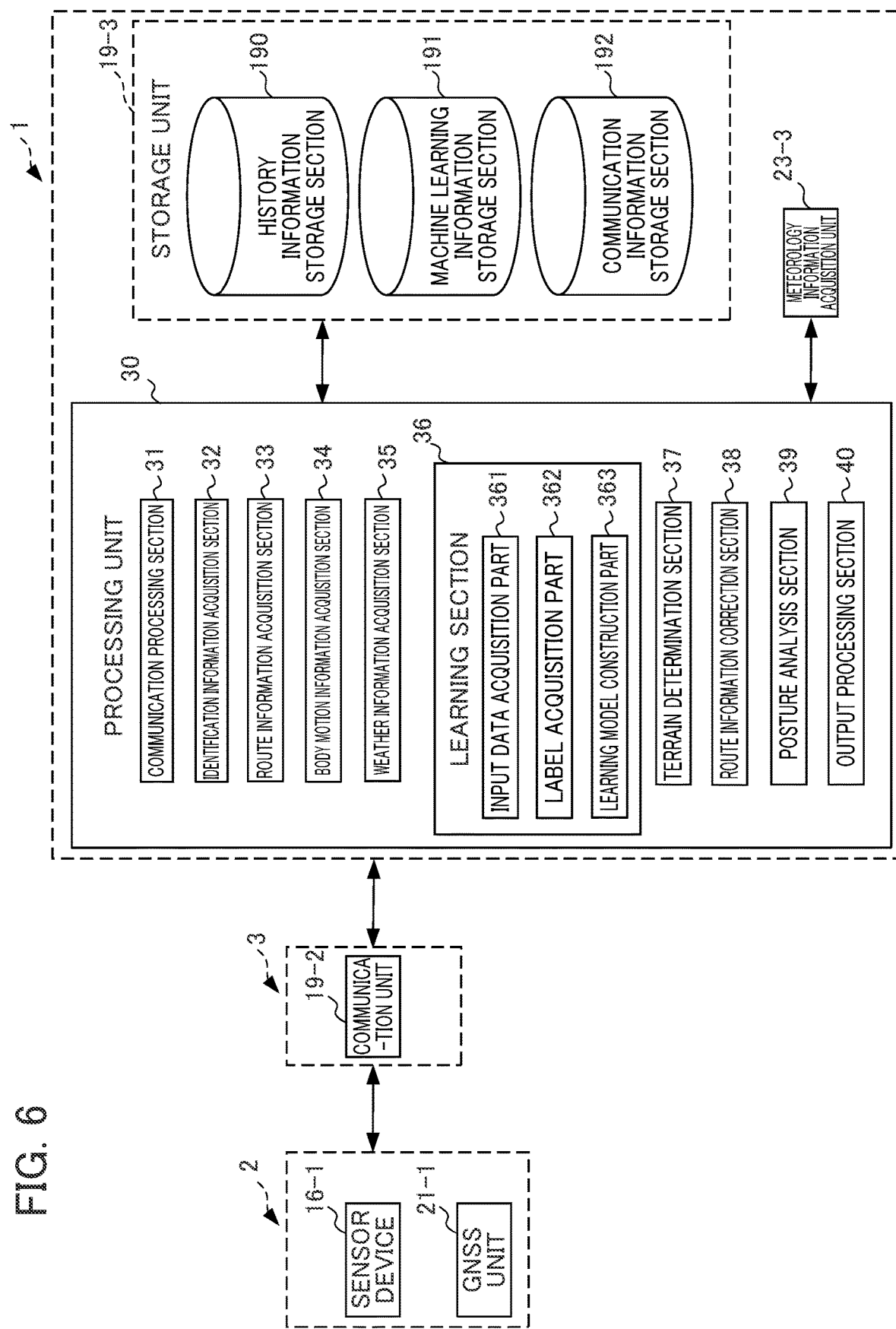
FIG. 6 is a functional block diagram showing a part of a functional configuration of a management server according to an embodiment of the present invention.

Next, the functional configuration of the management server 1 performing terrain sensing processing will be explained. FIG. 6 is a functional block diagram showing part of the functional configuration of the management server 1.

As shown in FIG. 6, a history information storage section 190 in which log data acquired from the plurality of sensor devices 2 and weather information associated with the log data is stored; a machine learning inform on storage section 191 in which a learning model described later or information related to raining data used for constructing learning model is stored; and a communication information storage section 192 in which information related to communication of the management server 1 is stored are established in one region of the storage unit 19-3.

The processing unit 30 performing various control of the management server 1 is realized by the CPU 11-3 executing arithmetic processing. The processing unit 30 of the present embodiment includes: a communication processing section 31, identification information acquisition section 32, route information acquisition section 33, body motion information acquisition section 34, weather information acquisition section 35, learning section 36, terrain sensing section route information correction section 38, posture analysis section 39, and output processing section 40.

The communication processing section 31 executes processing for communication with external devices via the communication unit 20-3. For example, the communication processing section 31 executes processing for transmitting various information with the user terminal 3 connected to the management server 1 or the sensor device 2 via the user terminal 3.

The identification information acquisition section 32 acquires identification information for identifying the sensor device 2, which is the sender of the log data. According to the identification information acquired from the identification information acquisition section 32, it is possible to identify the user wearing the sensor device 2.

The route information acquisition section 33 acquires the route information of the route on which the user wearing the sensor device 2 is moving, based on positioning data acquired by the GNSS unit 21-1 and sent via the communication unit 20-3. Route information is geographic positional information including the altitude, latitude, longitude information of the route on which the user is moving, etc.

The body motion information acquisition section 34 acquires the movement information of the user, based on movement data detected by the sensor unit 16-1, and sent from the sensor device 2 via the user terminal 3. More specifically, the body motion information acquisition section 34 acquires body motion information by analyzing the change in movement speed and change in movement direction of the user while walking or while running. As the body motion information of the user, the pitch, stride, slope of pelvis, movement amount of leg in vertical direction, ground contact time of leg, acceleration during kick-out, deceleration amount during ground contact of leg, etc. during a movement action such as walking or running of the user can be exemplified. Stride is the width of one step of the user during a movement action, and pitch is the number of steps per unit time such as cadence. In addition, the body motion information acquisition section 34 acquires body motion information as input data of the learning section 36.

An example of processing by the body motion information acquisition section 34 acquiring the slope of the pelvis caused by the posture of the user will be explained. The body motion information acquisition section 34 performs calibration for matching the slope of the sensor device 2 during upright posture and vertical direction, so that the slope of the pelvis corresponding to when the upright posture of the user wearing the sensor device 2 serves as a reference. Calibration is performed by maintaining the stand-by state for a predetermined time with a slope of the posture corresponding to the upright posture, using the angle formed by the gravitational acceleration and axis of the longitudinal direction of the device, so that the slope of the pelvis in an upright posture becomes the reference. In the case of the slope the pelvis of the user wearing the sensor device 2 making a slope corresponding to a forward-leaning posture, the sensor device 2 worn in the vicinity of the waist also slopes following this, and the slope making the forward-leaning posture is larger than the slope in the case of being the upright posture. A change in slope of the pelvis of the user is thereby acquired, and the posture change such as forward-leaning posture is acquired.

The weather information acquisition section 35 acquires the weather information from the meteorological information acquisition unit 23-3. The processing unit 30 stores the weather information acquired from the meteorological information acquisition unit 23-3 to ire associated with log data sent from the sensor device 2. More specifically, the processing unit 30 links identification information, route information and body motion information acquired by analyzing the same log data, and the corresponding weather information with each other, and stores as one set of history information in the history information storage section 190.

The learning section 36 constructs a learning model used for determining the terrain on which the user is moving, by performing supervised learning. The learning section 36 includes an input data acquisition part 361, label acquisition part 362, and learning model construction part 363.

The input data acquisition part 361 acquires body motion information of a plurality of different users moving on a route having terrain from the history information storage on 190, e.g., route which is known (hereinafter referred to as known route), as input data. The input data acquisition part 361 preferably acquires the input data related to a plurality of known routes having different terrain, and acquires the body motion information of a plurality of different users for every known route. It is thereby possible to specify with higher precision the correlation of terrain with the body motion information of the user. The body motion information acquired as the input data is preferably information in the case of the weather information being clear skies or cloudy. For example, in the case of the weather being rain or snow, the ground surface 5 of the route is wetted by rain or snow and mud is produced, and changes to a state in which the movement action by the user is difficult compared to while clear skies or while cloudy. By using only the body motion information of the user performing a movement action in a state in which the ground surface 5 of the route while clear skies or cloudy is dry as the input data, it is possible to eliminate the change in state of the ground surface 5 caused by weather. Consequently, it is possible to construct a learning model in which the correlation of terrain with body motion information of the user is more accurately reflected.

The label acquisition part 362 acquires the terrain of a known route as the label. As the terrain, for example, the slope of the route relative to a level surface such as uphill, downhill or level ground, the shape of the ground surface 5, etc. can be exemplified. As the shape of the ground surface 5 of the route, for example, a flat shape, step shape, uneven shape, etc. can be exemplified. As examples of terrain, terrain sloping upwards by a certain angle relative to the advancing direction of the user in which the ground surface 5 is a step shape, terrain sloping downwards by a certain angle relative to the advancing direction of the user in which the ground surface 5 is flat, level ground in which the ground surface 5 is an uneven shape, etc. can be exemplified. The terrain of known routes is obtained by the user inputting terrain data via the input unit 17-3 or the like, or acquired from a database of terrain or the like.

The learning model construction part 363 constructs a learning model for determining the terrain of a determination target route for which the terrain is unknown, performing supervised learning with the group of the input data acquired by the input data acquisition part 361 and the label acquired by the label acquisition part 362 as training data. Supervised learning learns a characteristic in these data sets by giving a group of the input data (input) and label (result) data to the learning section 36 in bulk, and is a model estimating the result from the input, and can be realized using a neural network or Support Vector Machine (hereinafter also called SVM).

The learning model construction part 363 causes the constructed learning model to be stored in the machine learning information storage section 191. It should be noted that the learning model construction part 363 preferably constructs a learning model using training data corresponding to a plurality of known routes having different terrain.

Herein, the relationship of the terrain which is the label with the body motion information which is the input data will be explained. For example, in the case of the terrain on which the user is moving being uphill, there is a tendency for the pitch to decline and the stride to become shorter compared to the case of the user moving on flat ground. Conversely, in the case of the terrain on which the user is moving being downhill, there a tendency for the pitch to increase and the stride to become greater. In addition, for example, in the case of the shape of the ground surface being a step shape, there is tendency for the movement amount of the leg in the vertical direction to be greater in uphill and smaller in downhill compared to a flat shape.

The terrain sensing section 37, for example, determines the terrain on which the user wearing the sensor device 2 is moving, based on the body motion information acquired by the body motion information acquisition section 34. More specifically, the terrain sensing section 37 determines the terrain on which this user is moving, by inputting the body motion information of the user during a movement action on the determination target terrain into the learning model constructed by the learning section 36.

The terrain sensing section 37 may select whether or not to perform determination of the terrain of the determination target route based on the body motion information, according to whether satisfying a body motion information use condition. For example, it may satisfy the body motion information use condition in the case of satisfying all of the following (a) to (c), may satisfy the body motion information use condition in the case of satisfying (a) and (b), or may satisfy the body motion information use condition in the case of satisfying only (c). It should be noted that, in the following explanation, a user for which this body motion information is used for terrain sensing processing by the terrain sensing section 37 is defined as "determination target user", a user other than the determination target user is defined as "other user", and in the case of explaining contents in common with the determination target user and other user, is defined as simply "user".

(a) history information of plurality of users having moved on the determination target route is stored in history information storage section 190

(b) body motion information of determination target user and body motion information at least predetermined number of other users exhibit common behavior in a specific segment in the determination target route (c) weather information during movement action of determination target user is clear skies or cloudy The specific segment, for example, may be a segment including a point at which the terrain changes from flat ground to uphill. When a runner in a normal state in which fatigue, etc. has not accumulated is approaching uphill from flat ground, there is a tendency for the pitch to decline and stride to become short. On the other hand, since a runner for which fatigue, etc. has accumulated is a state in which the pitch declines and the stride is short even on flat ground, a change in body motion in such a specific segment of the runner in the normal state hardly occurs. In other words, by confirming whether the body motion information of the determination target user in the above such specific segment exhibits behavior common with the body motion information of other users, it is possible to understand whether the determination target user is in a normal state.

The terrain sensing section 37 may determine the terrain of the determination target route using the body motion information acquired by the body motion information acquisition section 34, only in the case of satisfying the body motion information use condition. On the other hand, the terrain sensing section 37 may determine the terrain of the determination target route without using body motion information in the case of not satisfying the body motion information use condition, or may not perform determination processing of the terrain of the determination target route. In the case of determining the terrain without using body motion information, for example, the terrain of the determination target route may be defined as flat ground.

Herein, the body motion of the user during the movement action is not only caused by terrain, but also influenced by causes such as fatigue of the user during the movement action, state of the ground surface 5 with which the legs of the user make contact, etc. can be considered. For example, when fatigue of the user while running accumulates, there is a possibility of the pitch declining and the stride becoming shorter, as in the case of the terrain being uphill, even if the terrain is flat. In contrast, in the present embodiment, the terrain is determined using the body motion information only in the case of the body motion information of the determination target user in the specific segment exhibiting behavior common with the body motion information of other users. Since it is thereby possible to avoid determination of the terrain using the body motion information in the case of the body motion of the determination target user changing due to fatigue, it is possible to prevent misjudgment of the terrain. In addition, for example, if the ground surface 5 is wetted due to rain or snow and mud or the like is produced, it becomes difficult for the user to run, and influences the body motion of this user. In the present embodiment, since it is possible to avoid determination of terrain using the body motion information in the case of rain or snow, it is possible to prevent misjudgment of the terrain.

The route information correction section 38 corrects the route information of the determination target route acquired by the route information acquisition section 33 based on the terrain determined by the terrain sensing section 37. More specifically, the route information correction section 38 estimates the altitude based on the terrain determined by the terrain sensing section 37, and may decide the altitude of the determination target route based on the estimated estimation altitude, and the altitude included in the route information acquired by the route information acquisition section 33. For example, based on the comparison result of the estimation altitude and the altitude included in the route information acquired by the route information acquisition section 33 at the same point as the point at which the estimation altitude was estimated, the route information correction section 38 may decide the altitude of the above-mentioned point. In addition, the route information correction section 38 may decide the altitude based on the maximum value and minimum value for the altitude in the determination target route of the route information acquired by the route information acquisition section 33, and the difference between the maximum value and minimum value of the estimation altitude in the determination target route estimated from the terrain determined by the terrain determination section 37. For example, in the case of the route information acquisition section 33 acquiring route information in which the difference between the maximum value and minimum value for the altitude in the determination target route being established as 20 m, and the difference between the maximum value and minimum value for the estimation altitude in the determination target route being 10 m, the difference between the maximum value and minimum value for the altitude in the determination target route may be corrected as 15 m. Even if route information acquired based on positioning data is influenced by the radio wave environment, and error arises, it is thereby possible to correct based on the terrain determination using body motion information of the user making direct contact on the ground surface 5.

The posture analysis section 39 specifies the posture of the user based on the body motion information of this user, and determines the propriety of the posture during a movement action such as the walking form or running form of the user, based on the reference posture set in advance according to the type of movement action such as walking or running and the terrain, and the specified body motion information of the user. For example, the posture analysis section 39 may derive the posture of the user by analyzing the slope of the pelvis, pitch, stride, movement amount of legs in the vertical direction, etc. of the user during the movement action acquired by the body motion information acquisition section 34. For example, it may specify whether being posture in which the user stands upright, a leaning forward position, or the like from the slope of the pelvis included in the body motion information, and may specify the posture of the user during a movement action. In addition, the posture analysis section 39 specifies the reference posture based on the terrain determined by the terrain sensing section 37. The reference posture, for example, in the case of the terrain being uphill, sets the posture sloping more forward compared to a case of the terrain being flat ground as the reference posture. Then, the posture analysis section 39 determines the posture or the user cased on the comparison result between the posture of the user specified based on the body motion information and the specified reference posture. The posture analysis section 39 may determine that the posture during the movement action is better with a higher degree of similarity of the posture of the user relative to the reference posture, for example.

The output processing section 40 performs processing to output the route information of the determination target route acquired by the route information acquisition section 33 or route information of the determination target route corrected by the route information correction section 38, the terrain of the determination target route determined by the terrain sensing section 37, analysis results of posture during a movement action of the user by the posture analysis section 39, etc.

Construction Processing of Learning Model

Figure 7:
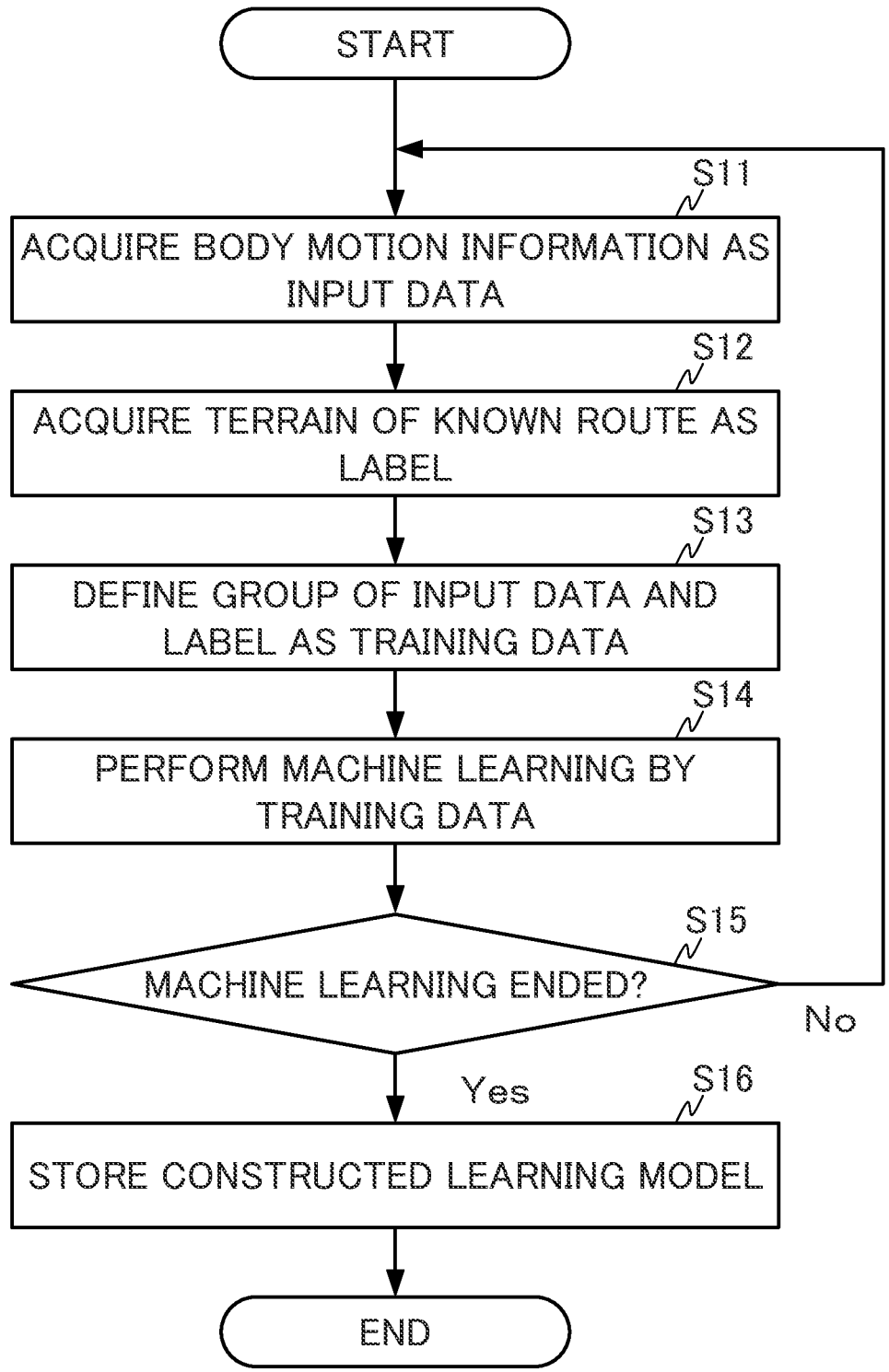
FIG. 7 is a flowchart showing an example of flow of construction processing of a learning model by a management server according to an embodiment of the present invention.

Next, operation during machine learning in the terrain sensing system S according to the present embodiment will be explained. FIG. 7 is a flowchart showing an example of the flow of construction processing of a learning model by the learning section 36 of the management server 1.

The input data acquisition part 361 of the learning section 36 acquires body motion information of the user during a movement action on a known route in the body motion information stored in the history information storage section 190 as the input data (Step S11).

The label acquisition part 362 acquires the terrain of the known route linked to the body motion information acquired in Step S11 among terrains stored in the history information storage section 190 as the label (Step S12).

The learning model construction part 363 accepts a group of the input data acquired in Step S11 and the label acquired in Step S12 as training data (Step S13).

The learning model construction part 363 executes machine learning using the training data accepted in Step S13 (Step S14).

After Step S14, the learning model construction section 363 determines whether to end machine learning or repeat machine learning (Step S15). The learning model construction part 363 returns the processing to Step S11 in the case of determining to repeat machine learning (Step S15; NO). Then, the management server 1 repeats the same operation. On the other hand, the learning model construction part 363 advances the processing to Step S16 in the case of determining to end the machine learning (Step 315: YES). It should be noted that the condition for ending machine learning can be decided arbitrarily. For example, it may be configured so as to end machine learning in the case of having repeated machine learning a number of times set in advance. More specifically, it may be configured so as to end machine learning in the case of executing machine learning using the training data obtained from at least a predetermined number of different determination users relative to each of at least a predetermined number of determination routes which are known routes.

The learning section 36 stores this learning model in the machine learning information storage section 191 (Step S16). It is thereby possible to extract a learning model from the machine learning information storage section 191, in the case of requiring a learning model for determination of the terrain from the terrain sensing section 37. In addition, in the case of acquiring new training data, it is also possible to perform further machine learning on the learning model.

Terrain Sensing Processing

Next, an example of terrain sensing processing by the terrain sensing system S will be explained while referencing the drawings. In the present terrain sensing processing, a case of the user performing running as the movement action will be explained as an example.

Figure 8:
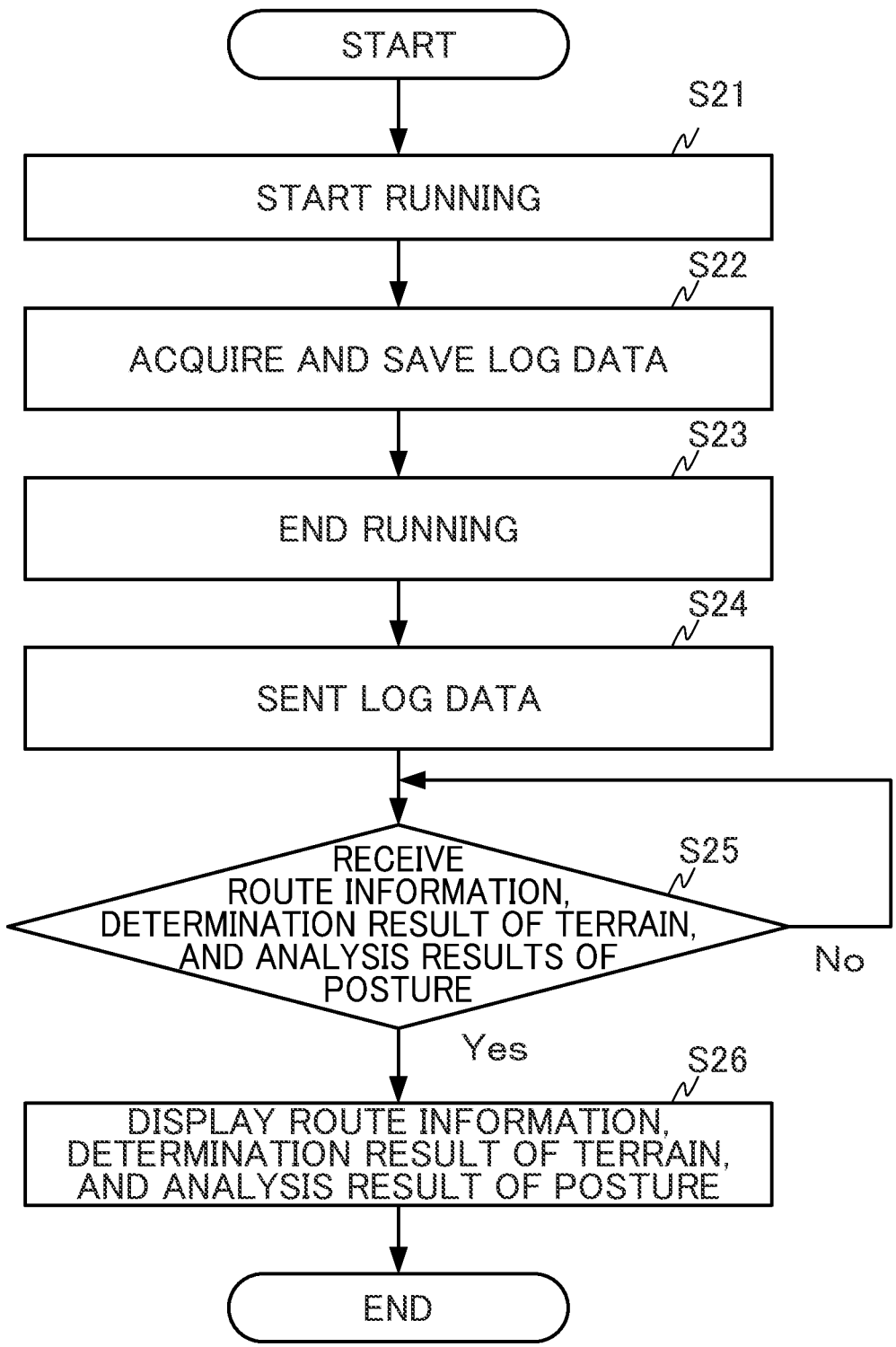
FIG. 8 is a flowchart showing an example of the flow of processing executed by a user terminal in terrain sensing processing executed by the terrain sensing system according to an embodiment of the present invention.

First, an example of the flow of processing mainly executed by the user terminal 3 will be explained by referencing FIG. 8. FIG. 8 is a flowchart showing an example of the flow of processing executed by the user terminal 3 in the terrain sensing processing executed by the terrain sensing system S.

First, the user carrying the user terminal 3 activates the sensor device 2, and starts running in a state wearing the sensor device 2 in the vicinity of the waist (Step S21). At this time, the user operates the input unit 17-1 to instruct detection start of log data by the sensor unit 16-1 and GNSS unit 21-1.

The user terminal 3 acquires and saves log data detected by the sensor device 2 (Step S22). More specifically, first, the CPU 11-1 of the sensor device 2 acquires movement data indicating the acceleration and angular speed of the sensor device 2 detected by the sensor unit 16-1, and positioning data of the sensor device 2 detected by the GNSS unit 21-1, and sends this movement data and positioning data to the user terminal 3. Then, the user terminal 3 acquires movement data and positioning data via the communication unit 20-2, and saves in the storage unit 19-3.

The user ends running (Step S23). At this time, the user operates the unit 17-1 to instruct detection end of log data by the sensor unit 16-1 and GNSS unit 21-1.

The CPU 11-2 of the user terminal 3 extracts log data saved in Step S22 from the storage unit 19-2, and sends to the management server 1 via the communication unit 20-2 (Step S24). The processing executed by the management server 1 will be described later.

The CPU 11-2 of the user terminal 3 determines whether receiving route information, determination results of terrain, and analysis results of running form described later sent from the management server (Step S25). The CPU 11-2 repeats the processing of Step S25 in the case of not receiving the route information, determination results of terrain and analysis results of running form from the management server 1 (Step S25: NO). On the other hand, the processing is advanced to Step S26 in the case of having received route information, determination results of terrain and analysis results of running form from the management server 1 (Step S2S: YES).

The CPU 11-2 of the user terminal 3 displays the route information, determination results of terrain and analysis results of running form from the management server 1 on the output unit 18-2 such as a display (Step S26). After the processing of Step S26, the processing executed by the user terminal 3 in the terrain sensing processing ends.

Figure 9:
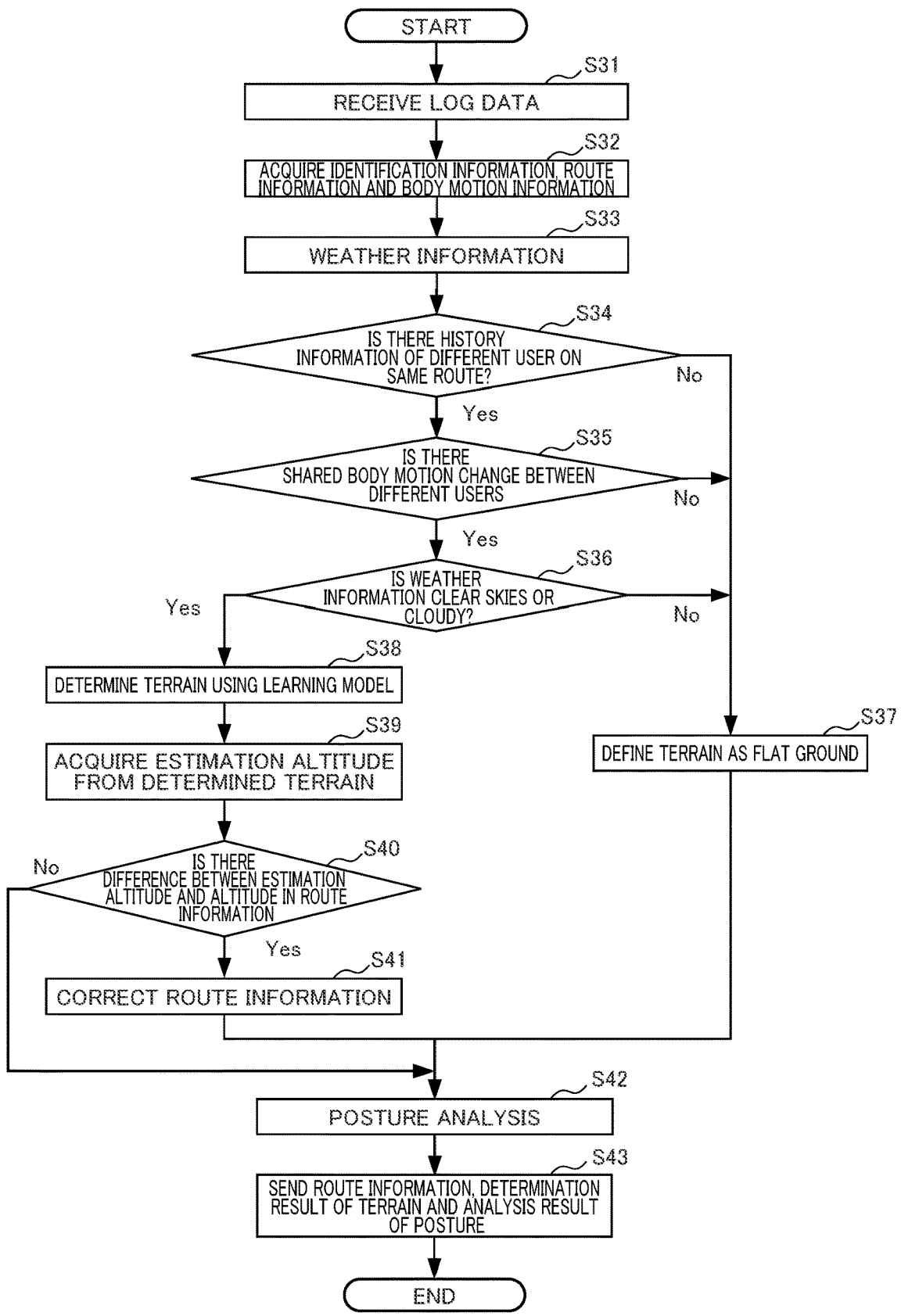
FIG. 9 is a flowchart showing an example of the flow of terrain sensing processing executed by a management server of a terrain sensing system according to an embodiment of the present invention.

Next, an example of the flow of processing executed by the management server 1 will be explained while referencing FIG. 9. FIG. 9 is a flowchart showing the flow of terrain sensing processing by the management server 1 of the terrain sensing system S.

As shown in FIG. 9, the communication processing section 31 of the management server 1 receives log data sent from the user terminal 3 in Step S24 (Step S31).

The processing unit 30 of the management server 1 acquires identification information, route information and body motion information from the log data received in Step S31 (Step S32). More specifically, identification information is acquired from the log data by the identification information acquisition section 32, route information is acquired from the log data by the route information acquisition section 33, and body motion information is acquired from the log data by the body motion information acquisition section 34. By acquiring route information by the route information acquisition section 33, the determination target route for which terrain is determined the terrain sensing system S is specified.

The weather information acquisition section 35 acquires weather information during a movement action of the determination target user on the determination target route from the meteorological information acquisition unit 23-3 (Step S33).

The terrain sensing section 37 determines whether history information acquired by other users other than the determination target user running on the determination target route is being stored in the history information storage section 190 (Step S34). The terrain sensing section 37 advances the processing to Step S37 in the case of history information of other users having run on the determination target route not being stored (Step S34: NO). Then the terrain sensing section 37 determines the terrain of the determination target route as flat level ground in which the ground surface 5 is smooth (Step S37). On the other hand, the terrain sensing section 37 causes the processing to advance to Step S35 in the case of history information of other users having run on the determination target route being stored (Step S34: YES).

The terrain sensing section 37 determines whether there is a change in the body motion information shared between the determination target user and other users in Step S31 in a specified segment in the determination target route (Step S35). The terrain sensing section 37 causes the processing to advance to Step S37 in the case of there not being a change in the body motion information shared between the determination target user and other users in a specified segment in the determination target route (Step S35: NO). Then, the terrain sensing section 37 determines the terrain of the determination target terrain as a flat ground in which the ground surface is smooth (Step S37). On the other hand, the terrain sensing section 37 causes the processing to advance to Step S36 in the case of there being a change in the body motion information shared between the determination target user and other users in a specified segment in the determination target route (Step S35: YES).

The terrain sensing section 37 determines whether the weather information acquired in Step S33 is clear skies or cloudy (Step S36). The terrain sensing section 37 causes the processing to advance to Step S37 in the case of the weather information acquired in Step S33 not being clear skies or cloudy (Step S36: NO). Then, the terrain sensing section 37 determines the terrain of the determination target route as flat ground in which the ground surface 5 is smooth (Step S37). On the other hand, the terrain sensing section 37 causes the processing to advance to Step S38 in the case of the weather information acquired in Step S33 being clear skies or cloudy.

Next, the terrain sensing section 37 determines the terrain of the determination target route using the learning model stored in the machine learning information storage section 191 (Step S38). More specifically, the terrain sensing section 37 determines the terrain of the determination target route by inputting the body motion information acquired in Step S32 into the learning model stored in the machine learning information storage section 191.

The route information correction section 38 acquires the estimation altitude of the determination target route calculated based on the terrain determined in Step S38 (Step S39).

The route information correction section 38 determines whether there a difference between the estimation altitude acquired in Step S39 and altitude of the route information acquired in Step S32 (Step S40). The route information correction section 38 causes the processing to advance to Step S41 in a case there being a difference between the estimation altitude and the altitude of the route information (Step S40: YES). Then, the route information correction section 38 corrects the route information acquired in Step S32 using the estimation altitude acquired in Step S39 (Step S41), and causes the processing to advance to Step S42. On the other hand, the route information correction section 38 causes the processing to advance to Step S42 without going through Step S41, in the case of there not being a difference between the estimation altitude and altitude of the route information (Step S40: NO).

The posture analysis section 39 analyzes the running form of the determination target user based on the terrain determined in Step S37 or Step S38, the body motion information acquired in Step S32, the reference posture specified based on the terrain determined in Step S37 or Step S38, and determines the propriety of the running form (Step S42). More specifically, the posture analysis section 39 first specifies the posture of the user based on the body motion information of this user acquired in Step S32, and specifies the reference posture decided in advance based on the terrain determined in Step S37 or Step 38. Then, the posture analysis section 39 determines the propriety of the posture during the movement action of the user by comparing between the posture of the specified user and the specified reference posture.

The output processing section 40 sends the route information acquired in Step S32 or route information corrected in Step S41, the terrain determined in Step S37 or Step S38, and analysis results of the running form analyzed in Step S42 to the user terminal 3 (Step S43). After the processing of Step S43, the processing executed by the management server 1 in the terrain sensing processing ends.

As explained above, the management server 1 serving as an electronic device includes the processing unit 30 which acquires the body motion information of the user when the user is doing a movement action, and determines the terrain on which the user is moving based on the acquired body motion information. It should be noted that the management server 1 serving as an electronic device is sufficient so long as acquiring body motion information of the user for a user in a movement action, and may acquire the body motion information of the user when the user does a movement action. In addition, the processing unit 30 is sufficient so long as determining the terrain for the user in movement, and may be configured so as to determine the terrain on which the user moved.

Due to determining terrain from the body motion information in which the motion of the legs of the user making direct contact with the ground surface 5 is reflected, it is thereby possible to determine terrain with higher precision. More specifically, it is possible to determine more detailed terrain including the shape such as a step shape or uneven shape of the ground surface 5, not only the slope obtained from the altitude difference in a predetermined segment or the like.

In addition, in the present embodiment, the body motion information includes at least one among the pitch, stride, slope of the pelvis, movement amount of leg in vertical direction, ground contact time of leg, acceleration during kick-out, and deceleration amount during ground contact of the leg in the movement action of the user.

It is thereby possible to determine detailed information of the terrain with higher precision.

In addition, in the present embodiment, the processing unit 30 specifies the posture of the user based on the body motion information, specifies the reference posture based on the determined terrain, and determines the posture of the user based on the reference posture and the posture of the user.

Due to specifying the reference posture based on the terrain determined with high precision, it is thereby possible to more accurately determine the propriety of the posture during a movement action of the user according to the terrain.

In addition, in the present embodiment, the processing unit 30 acquires the body motion information of a plurality users in a movement action on a certain route as input data, acquires the terrain of the certain route as a label, and determines the terrain on which this user is moving based on the learning model constructed by performing supervised learning with the group of the input data and the label as training data, and the body motion information acquired separately from the training data.

Due to using the body motion information of a plurality of users, it is thereby possible to construct a learning model reflecting a more generalized relationship of terrain with body motion information, and possible to efficiently determine with higher precision the terrain.

In addition, in the present embodiment, the processing unit 30 selects whether to determine the terrain based on the body motion information based on whether or not the body motion information of a user in a movement action on the determination target route and the body motion information of a user in a movement action on the determination target route other than this user exhibit shared behavior in a specified segment in the determination target route.

It is thereby possible to prevent misjudgment of the terrain. For example, there are cases where the body motion of the determination target user in a movement action changes due to fatigue of the determination target user, even in the case of moving on the same terrain. In the case of determining terrain from the body motion information of the determination target user for which fatigue has accumulated, the body motion information changes due to the factor of fatigue, and there is concern over misjudgment of the terrain arising. In the present embodiment, due to selecting whether to determine terrain using the body motion information according to whether or not the body motion information of the determination target user and other users exhibit shared behavior, it is possible to prevent misjudgment of terrain from a change in body motion caused by fatigue of the determination target user or the like.

In addition, in the present embodiment, the processing unit 30 selects whether or not determining terrain based on the body motion information based on the weather information while the user is making a movement action.

It is thereby possible to prevent misjudgment by a change in the state of the ground surface 5 caused by weather.

In addition, in the present embodiment, based on the estimation altitude estimated based on the determined terrain, and the altitude based on the positioning satellite signals received from outside at the same point as the point at which the estimation altitude was estimated, the processing unit 30 decides the altitude of the above-mentioned point.

It is thereby possible to decide the altitude of the route using the altitude estimated from the terrain determined based on the body motion information together with the altitude based on the positioning satellite signals. Consequently, for example, even in a case of the route information being acquired based on the positioning satellite signal influenced by the radio wave environment and in which error occurred, it is possible to correct with more accurate altitude based on the determination results of terrain obtained using the body motion information of the user actually moving on the route.

It should be noted that the present invention is not to be limited to the aforementioned embodiment, and that modifications, improvements, etc. within a scope which can achieve the object of the present invention are also encompassed by the present invention.

In the aforementioned embodiment, the terrain sensing section 37 selects whether to determine the terrain of the determination target route based on the body motion information according to whether or not satisfying the body motion information use condition; however, it may determine the terrain based on the body motion information irrespective of whether satisfying the body motion information use condition.

In addition, in the aforementioned embodiment, the learning model for determining terrain is constructed by the learning section 36 performing supervised learning with the group of the body motion information which the input data and the terrain which is the label; however, it may include weather information as input data. In other words, the processing unit 30 may further acquire weather information during the movement action of a plurality of different users on a certain route as input data, and may determine the terrain on which this user is moving based on the learning model, the body motion information of the user during the movement action on the determination target route, and weather information while this user is making the movement action on the determination target route. More specifically, the input data acquisition section 361 may acquire weather information together with body motion information, and the learning model construction part 363 may construct a learning model for determining the terrain of the determination target route, by performing supervised learning with the group of the body motion information and weather information which is input data and the terrain which is the label as the training data. Then, the terrain sensing section 37 may determine the terrain of the determination target route, by inputting the weather information together with the body motion information to the learning model.

It is thereby possible to determine the terrain by taking account of the state of the ground surface 5 of the determination target route on which the user is moving. For example, if the ground surface 5 gets wet from rain or snow and mud, etc. is produced, it is difficult for the user to move on this ground surface 5, and influences the body motion of this user. In contrast, due to constructing the learning model using the weather information together with body motion information, it possible to determine the terrain taking account of the situation in which mud, etc. is produced on the ground surface 5 due to rain or snow and it is difficult for the user to move.

In addition, for example, the learning section 36 may include information indicating the propriety of the posture during a movement action of the user together with the terrain as a label. In other words, the processing unit 30 may further acquire comparison information between the reference posture set according to the terrain and the posture of the user during a movement action on a certain route, and may determine the terrain on which this user is moving and determine the comparison information between the reference posture and the posture of this during a movement action on the determination target route, based on the learning model and body motion information of the user during a movement action on the determination target route. More specifically, the label acquisition part 362 may acquire the comparison information between the reference posture and the posture of the user during a movement action on the route which is known together with the terrain, and may construct the learning model for determining the terrain of the determination target route and the propriety of the posture of the user moving on this route, by the learning model construction part 363 performing supervised learning with the group of the body motion information which is input data, and the terrain and the above-mentioned comparison information which are the label as training data. Then, the posture analysis section 39 may determine the comparison information between the above-mentioned reference posture and the posture of this user during a movement action, by inputting the body motion information of the user into the learning model.

It is thereby possible to efficiently determine the propriety of the posture during a movement action of the user together with the terrain of the route on which the user moved. For example, in the case of determining that the terrain is step-like uphill by the terrain determination section 37, it is possible to determine the propriety of the running form of the user relative to this terrain of step-like uphill.

In addition, for example, the learning section 36 may acquire the body motion information of the user during a movement action as input data, acquire evaluation results indicating the terrain and the propriety of the posture of this user as a label, and may construct a learning model for determining the terrain of the determination target route and the propriety of the posture of the user moving on this terrain, by performing supervised learning with the group of the body motion information which is input data and evaluation results of the terrain and posture which is the label as the training data. Then, the posture analysis section 39 may establish a configuration determining the terrain on which this user is moving and the evaluation results of the posture of the user at this time, by inputting the body motion information of the user to the learning model.

In addition, in the aforementioned embodiment, the management server 1 as an electronic device performing the terrain sensing processing constructs the learning model; however, a separate device from the electronic device such as the management server 1 may construct the learning model. Then, the management server 1 may execute terrain sensing using the learning model received from the above-mentioned separate device.

In addition, in the aforementioned embodiment, the management server 1 establishes an electronic device including the processing unit 30 performing the terrain sensing processing; however, at least either of the sensor device 2 and user terminal 3 may be established as an electronic device including the processing unit 30 performing the terrain sensing processing, or all of the management server 1, sensor device 2 and user terminal 3 may establish the configuration performing the terrain sensing processing.

In addition, in the aforementioned embodiment, the terrain sensing section 37 performs determination of the terrain based on the body motion information and learning model in the case of satisfying the body motion information use condition; however, a calculation formula may be created based on the correlation between the body motion information and terrain without using the learning model, and the terrain may be determined with this calculation formula. In this case, the terrain sensing section 37 may determine terrain by a calculation formula created based on the correlation between body motion information and terrain regardless of whether satisfying the body motion information use condition.

The processing sequence described above can be executed by hardware, and can also be executed by software. In other words, the functional configuration of FIG. 6 is merely an illustrative example, and the present invention is not particularly limited thereto. More specifically, the types of functional blocks employed to realize the above-described functions are not particularly limited to the examples shown in FIG. 6, so long as the management server 1 can be provided with the functions enabling the aforementioned processing sequence to be executed in its entirety.

In addition, a single functional block may be configured by a single piece of hardware, a single installation of software, or a combination thereof. The functional configurations of the present embodiment are realized by a processor executing arithmetic processing, and processors that can be used for the present embodiment include a unit configured by a single unit of a variety of single processing devices such as a single processor, multi-processor, multi-core processor, etc., and a unit in which the variety of processing devices are combined with a processing circuit such as ASIC (Application Specific Integrated Circuit) or FPGA (Field-Programmable Gate Array).

In the case of having the series of processing executed by software, the program constituting this software is installed from a network or recording medium to a computer or the like. The computer may be a computer equipped with dedicated hardware. In addition, the computer may be a computer capable of executing various functions, e.g., a general purpose personal computer, by installing various programs.

The storage medium containing such a program can not only be constituted by the removable medium distributed separately from the device main body for supplying the program to a user, but also can be constituted by a storage medium or the like supplied to the user in a state incorporated in the device main body in advance. The removable medium is composed of, for example, a magnetic disk (including a floppy disk), an optical disk, a magnetic optical disk, or the like. The optical disk is composed of, for example, a CD-ROM (Compact Disk-Read Only Memory), a DVD (Digital Versatile Disk), Blu-ray (Registered Trademark) or the like. The magnetic optical disk is composed of an MD (Mini-Disk) or the like. The storage medium supplied to the user in a state incorporated in the device main body in advance is constituted by, for example, the ROM 12-1 of FIG. 3, the ROM 12-2 of FIG. 4, or the ROM 12-3 of FIG. 5 in which the program is recorded or a hard disk included in the storage unit 19-1 of FIG. 3, the storage unit 19-2 of FIG. 4, or the storage unit 19-3 of FIG. 5, etc.

It should be noted that, in the present specification, the steps defining the program recorded in the storage medium include not only the processing executed in a time series following this order, but also processing executed in parallel or individually, which is not necessarily executed in a time series.

The embodiments of the present invention described above are only illustrative, and are not to limit the technical scope of the present invention. The present invention can assume various other embodiments. Additionally, it is possible to make various modifications thereto such as omissions or replacements within a scope not departing from the spirit of the present invention. These embodiments or modifications thereof are within the scope and the spirit of the invention described in the present specification, and within the scope of the invention recited in the claims and equivalents thereof.

What is claimed is:

1. An electronic device comprising a processing unit which executes processing comprising:
    performing calibration by associating a vertical direction with a slope of the electronic device in a state in which a user wearing the sensor device is in an upright posture, and setting the slope associated with the vertical direction as a reference slope;
    acquiring body motion information of the user during a movement action by the user;
    determining terrain during movement by the user, based on the acquired body motion information of the user;
    specifying a posture of the user based on (i) the acquired body motion information of the user and (ii) the reference slope set by performing the calibration;
    specifying a target reference posture based on the terrain having been determined; and
    determining a state of the posture of the user based on a difference between (i) the target reference posture and (ii) the posture of the user having been specified.

2. The electronic device according to claim 1, wherein the processing unit executes processing comprising:
    acquiring the body motion information of a plurality of the users during a movement action on a certain route as input data;
    acquiring terrain of the certain route as a label; and
    determining terrain on which the user is moving during the movement by the user, based on (i) a learning model constructed by performing supervised learning with a group of the input data and the label as training data, and (ii) the acquired body motion information of the user acquired separately from the training data.

3. The electronic device according to claim 2, wherein the processing unit executes processing comprising:
    further acquiring weather information during a movement action of a plurality of the users on the certain route as input data; and
    determining terrain on which the user is moving during the movement by the user, based on (i) the learning model, (ii) the acquired body motion information of the user during a movement action on a determination target route, and (iii) the weather information, while the user is making a movement action on the determination target route.

4. The electronic device according to claim 2, wherein the processing unit executes processing comprising:
further acquiring comparison information between the target reference posture specified based on the terrain and the posture of the user during a movement action on the certain route as the label; and
determining terrain on which the user is moving and determining comparison information between the target reference posture and the posture of the user during a movement action on a determination target route, based on the learning model and the body motion information of the user during a movement action on the determination target route.

5. The electronic device according to claim 1, wherein the body motion information includes at least one of a pitch, a stride, a slope of a pelvis, a movement amount of a leg in the vertical direction, a ground contact time of a leg, an acceleration during kick-out, and a deceleration amount during ground contact of a leg, during a movement action of the user.

6. The electronic device according to claim 1, wherein the processing unit executes processing comprising:
selecting whether to determine terrain based on the body motion information, based on whether the body motion information of the user during a movement action on a determination target route and the body motion information of a user other than the user during a movement action on the determination target route exhibit shared behavior in a specific segment in the determination target route.

7. The electronic device according to claim 1, wherein the processing unit executes processing comprising:
selecting whether to determine terrain based on the body motion information, and weather information during a movement action by the user.

8. The electronic device according to claim 1, wherein the processing unit executes processing comprising:
deciding an altitude of a point based on an estimation altitude estimated based on a determined terrain, and an altitude based on a positioning satellite signal received from outside of the point which is the same as the point at which the estimation altitude was estimated.

9. An electronic device comprising a processing unit which executes processing comprising:
performing calibration by associating a vertical direction with a slope of the electronic device in a state in which a user wearing the sensor device is in an upright posture, and setting the slope associated with the vertical direction as a reference slope;
acquiring body motion information of the user during a movement action by the user;
acquiring the body motion information of a plurality of the users during a movement action on a certain route as input data;
acquiring terrain of the certain route as a label;
determining terrain on which the user is moving during movement by the user, based on (i) a learning model constructed by performing supervised learning with a group of the input data and the label as training data, and (ii) the acquired body motion information of the user acquired separately from the training data;
specifying a posture of the user based on (i) the acquired body motion information of the user and (ii) the reference slope set by performing the calibration;
specifying a target reference posture based on the terrain having been determined; and
determining a state of the posture of the user based on a difference between (i) the target reference posture and (ii) the posture of the user having been specified.

10. The electronic device according to claim 9, wherein the processing unit executes processing comprising:
further acquiring weather information during a movement action of a plurality of the users on the certain route as input data; and
determining terrain on which the user is moving during the movement by the user, based on (i) the learning model, (ii) the acquired body motion information of the user during a movement action on a determination target route, and (iii) the weather information, while the user is making a movement action on the determination target route.

11. The electronic device according to claim 9, wherein the processing unit executes processing comprising:
further acquiring comparison information between the target reference posture specified based on the terrain and the posture of the user during a movement action on the certain route as the label; and
determining terrain on which the user is moving and determining comparison information between the target reference posture and the posture of the user during a movement action on a determination target route, based on the learning model and the body motion information of the user during a movement action on the determination target route.

12. The electronic device according to claim 9, wherein the processing unit executes processing comprising:
selecting whether to determine terrain based on the body motion information, based on whether the body motion information of the user during a movement action on a determination target route and the body motion information of a user other than the user during a movement action on the determination target route exhibit shared behavior in a specific segment in the determination target route.

13. The electronic device according to claim 9, wherein the processing unit executes processing comprising:
selecting whether to determine terrain based on the body motion information, and weather information during a movement action by the user.

14. The electronic device according to claim 9, wherein the processing unit executes processing comprising:
deciding an altitude of a point based on an estimation altitude estimated based on a determined terrain, and an altitude based on a positioning satellite signal received from outside of the point which is the same as the point at which the estimation altitude was estimated.

15. An electronic device comprising a processing unit which executes processing comprising:
performing calibration by associating a vertical direction with a slope of the electronic device in a state in which a user wearing the sensor device is in an upright posture, and setting the slope associated with the vertical direction as a reference slope;
acquiring body motion information of the user during a movement action by the user;
determining terrain during movement by the user, based on the acquired body motion information of the user;

deciding an altitude of a point based on an estimation altitude estimated based on a determined terrain, and an altitude based on a positioning satellite signal received from outside of the point which is the same as the point at which the estimation altitude was estimated;

specifying a posture of the user based on (i) the acquired body motion information of the user and (ii) the reference slope set by performing the calibration;

specifying a target reference posture based on the terrain having been determined; and determining a state of the posture of the user based on a difference between (i) the target reference posture and (ii) the posture of the user having been specified.

16. A non-transitory computer-readable storage medium storing a program that is executed by a computer that comprises a processor to control an electronic device, the program being executable to cause the computer to perform operations comprising:

performing calibration by associating a vertical direction with a slope of the electronic device in a state in which a user wearing the sensor device is in an upright posture, and setting the slope associated with the vertical direction as a reference slope;

acquiring body motion information of the user during a movement action by the user;

determining terrain during movement by the user, based on the acquired body motion information of the user;

specifying a posture of the user based on (i) the acquired body motion information of the user and (ii) the reference slope set by performing the calibration;

specifying a target reference posture based on the terrain having been determined; and determining a state of the posture of the user based on a difference between (i) the target reference posture and (ii) the posture of the user having been specified.

17. A terrain sensing method executed by an electronic device, the method comprising:

performing calibration by associating a vertical direction with a slope of the electronic device in a state in which a user wearing the sensor device is in an upright posture, and setting the slope associated with the vertical direction as a reference slope;

acquiring body motion information of the user during a movement action by the user;

determining terrain during movement by the user, based on the acquired body motion information of the user;

specifying a posture of the user based on (i) the acquired body motion information of the user and (ii) the reference slope set by performing the calibration;

specifying a target reference posture based on the terrain having been determined; and determining a state of the posture of the user based on a difference between (i) the target reference posture and (ii) the posture of the user having been specified.

* * * * *

UNITED STATES PATENT AND TRADEMARK OFFICE
CERTIFICATE OF CORRECTION

PATENT NO. : 12,339,415 B2
APPLICATION NO. : 17/894883
DATED : June 24, 2025
INVENTOR(S) : Takehiko Kii Page 1 of 1

It is certified that error appears in the above-identified patent and that said Letters Patent is hereby corrected as shown below:

In the Claims

Column 19, Line 40, Claim 7, delete "information," and insert -- information --.

Column 20, Line 48, Claim 13, delete "information," and insert -- information --.

Signed and Sealed this
Twenty-sixth Day of August, 2025

Coke Morgan Stewart
*Acting Director of the United States Patent and Trademark Office*